(12) United States Patent
Abbasi (10) Patent No.: US 9,655,654 B2
(45) Date of Patent: May 23, 2017

(54) SPINAL ROD SUPPORT STRUCTURE WITH CLAMP

(71) Applicant: Hamid R Abbasi, Edina, MN (US)

(72) Inventor: Hamid R Abbasi, Edina, MN (US)

(73) Assignee: Advance Research System, LLC, Edina, MN (US)

( * ) Notice: Subject to any disclaimer, the term of this patent is extended or adjusted under 35 U.S.C. 154(b) by 0 days.

(21) Appl. No.: 15/142,517

(22) Filed: Apr. 29, 2016

(65) Prior Publication Data

US 2016/0242817 A1     Aug. 25, 2016

Related U.S. Application Data

(62) Division of application No. 14/043,510, filed on Oct. 1, 2013.

(51) Int. Cl.
*A61B 17/56* (2006.01)
*A61B 17/70* (2006.01)

(52) U.S. Cl.
CPC ...... *A61B 17/7032* (2013.01); *A61B 17/7049* (2013.01)

(58) Field of Classification Search
CPC .............. A61B 17/7032; A61B 17/7049
See application file for complete search history.

(56) References Cited

U.S. PATENT DOCUMENTS

| | | | |
|---|---|---|---|
| 5,334,203 A * | 8/1994 | Wagner | A61B 17/7052 24/396 |
| 5,609,593 A | 3/1997 | Errico et al. | |
| 6,273,914 B1 | 8/2001 | Papas | |
| 6,379,354 B1 | 4/2002 | Rogozinski | |
| 6,783,526 B1 | 8/2004 | Lin | |
| 7,833,248 B2 | 11/2010 | Markworth et al. | |
| 7,935,134 B2 | 5/2011 | Reglos | |
| 8,066,739 B2 | 11/2011 | Jackson | |
| 8,070,785 B2 | 12/2011 | Biscup | |
| 8,118,837 B2 | 2/2012 | Lemoine | |
| 8,152,810 B2 | 4/2012 | Jackson | |
| 8,167,914 B1 | 5/2012 | Hunt et al. | |
| 8,182,514 B2 | 5/2012 | Gimbel | |
| 8,197,512 B1 | 6/2012 | Hunt et al. | |
| 8,273,089 B2 | 9/2012 | Jackson | |
| 8,308,776 B2 * | 11/2012 | Abdou | A61B 17/8685 606/279 |
| 8,337,532 B1 * | 12/2012 | McLean | A61B 17/7011 606/250 |
| 8,357,184 B2 | 1/2013 | Woolley | |
| 8,617,585 B2 | 12/2013 | Boden | |
| 8,758,411 B1 | 6/2014 | Rayon et al. | |
| 9,023,087 B2 | 5/2015 | Frankel et al. | |

(Continued)

*Primary Examiner* — Mary Hoffman
(74) *Attorney, Agent, or Firm* — Christensen, Fonder, Dardi & Herbert PLLC (57) ABSTRACT

The present application discloses an implantable device for spinal treatment or stabilization. The device includes a spinal rod support and gripping jaws. The gripping jaws operate between an opened position and a closed position to grip and release a first spinal rod implanted into a patient. The spinal rod support includes a perimeter structure having an interior cavity and passage to connect a second spinal rod to the device to operably connect the first and second spinal rods through the implantable device to form a spinal stabilization structure.

15 Claims, 7 Drawing Sheets

(56) References Cited

U.S. PATENT DOCUMENTS

| | | | |
|---|---|---|---|
| 2003/0004512 A1 | 1/2003 | Farris et al. | |
| 2005/0240265 A1 | 10/2005 | Kuiper et al. | |
| 2006/0089662 A1 | 4/2006 | Davison | |
| 2007/0043365 A1 | 2/2007 | Ritland | |
| 2007/0161985 A1 | 7/2007 | Demakas | |
| 2007/0198014 A1 | 8/2007 | Graf et al. | |
| 2007/0233091 A1 | 10/2007 | Naifeh et al. | |
| 2007/0233123 A1 | 10/2007 | Ahmad | |
| 2007/0250061 A1 | 10/2007 | Chin | |
| 2007/0276384 A1* | 11/2007 | Spratt | A61B 17/7056 606/276 |
| 2008/0082112 A1* | 4/2008 | Lawton | A61B 17/705 606/151 |
| 2009/0036929 A1 | 2/2009 | Reglos et al. | |
| 2009/0099604 A1* | 4/2009 | Cho | A61B 17/7049 606/250 |
| 2009/0210007 A1* | 8/2009 | Levy | A61B 17/7052 606/246 |
| 2010/0030135 A1 | 2/2010 | Mitchell | |
| 2010/0049252 A1 | 2/2010 | Smisson | |
| 2010/0256683 A1 | 10/2010 | Iott | |
| 2010/0274295 A1 | 10/2010 | Carls et al. | |
| 2010/0298884 A1 | 11/2010 | Faizan et al. | |
| 2010/0318130 A1 | 12/2010 | Parlato | |
| 2011/0087287 A1 | 4/2011 | Reeder, Jr. et al. | |
| 2011/0288599 A1 | 11/2011 | Michielli | |
| 2011/0307013 A1 | 12/2011 | Winslow | |
| 2012/0116458 A1 | 5/2012 | Van Nortwick | |
| 2013/0053901 A1 | 2/2013 | Cormier | |
| 2013/0253473 A1 | 9/2013 | Nebosky | |
| 2015/0094769 A1 | 4/2015 | Abbasi | |

\* cited by examiner

SPINAL ROD SUPPORT STRUCTURE WITH CLAMP

CROSS-REFERENCE TO RELATED APPLICATION

This application is a divisional application of U.S. application Ser. No. 14/043,510 filed Oct. 1, 2013 and entitled SYSTEM AND METHOD FOR LENGHTING AN EXISTING SPINAL SUPPORT STRUCTURE, the disclosure of which is hereby incorporated by reference into the present application.

BACKGROUND

The present disclosure relates to spinal fusion surgery and more particularly pertain to a new system and method for lengthening an existing spinal support structure for facilitating a surgical procedure for revising by extending a previous spinal support construct used, for example, for spinal vertebral fusion.

Conventional spine surgeries, such as spinal fusion surgery, involves the installation of a rod connected to screws mounted on individual spinal vertebrae, and in the past required forming an incision in the tissue of the patient that extended for at least the distances between the most distant vertebrae to which the rod was to be mounted, and typically at least the length of the rod to be installed. More recently, a minimally invasive technique has been developed and used in which a number of smaller incisions are formed in the back, rather than the traditional single long incision, with each incision generally corresponding to one of the locations of the pedicle screw to be placed. One or more additional incisions may be formed to permit lengthwise insertion of the rod into a position that is adjacent to the screw, so that the rod may be attached to the previously mounted screws.

SUMMARY

In one aspect, the present disclosure relates to a system for interfacing a first support rod to a second support rod, and may comprise a rod interface device configured to receive a portion of a first support rod and grip a portion of a second support rod to secure the second support rod to the first support rod. The rod interface device may comprise a frame having a bottom wall and a perimeter wall extending from the bottom wall to partially define an interior configured to receive a portion of the first support rod therein. The rod interface device may also comprise a pair of gripping jaws movably mounted on the frame such that the gripping jaws are movable with respect to each other between a gripping position in which the second rod is gripped by the jaws and a release position in which the second rod is released from any grip of the gripping jaws.

In another aspect, the disclosure relates to a system for interfacing first support rod to a second support rod, and may comprise a screw interface device configured to receive a portion of a first support rod and being configured to mount on a head portion of a screw. The screw interface device may comprise a screw mount element configured to be removably mounted on the head portion of the screw, the screw mount element being insertable into the cavity to secure the second support rod in the cavity. The screw interface device may also comprise a rod mount element mounted on the screw mount element, with the rod mount element defining a pocket for receiving a portion of the first support rod.

In yet another aspect, the disclosure relates to a spinal support construct that may comprise a primary spine stabilization structure which may include a pair of primary pedicle screws each configured for threaded insertion into a vertebra of the patient, with each of the primary pedicle screws including a threaded body portion and a head portion defining a cavity. The primary spine stabilization structure may further include a primary rod extending into the cavities of the primary pedicle screws. The construct may also comprise a secondary spine stabilization structure which may include a secondary pedicle screw configured for threaded insertion into a vertebra of the patient, with the secondary pedicle screws including a threaded body portion and a head portion defining a cavity. The secondary spine stabilization structure may include a secondary rod having a portion positioned in the cavity of the secondary pedicle screw and extending to the primary spine stabilization structure, and an interface structure linking the secondary rod to the primary spine stabilization structure.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of the construction and to the arrangements of the components, as well as the particulars of the steps, set forth in the following description or illustrated in the drawings. The disclosure is capable of other embodiments and implementations and is thus capable of being practiced and carried out in various ways. Also it is be understood that the phraseology and terminology employed herein are for the purpose of description and should not be regarded as limiting.

As such, those skilled in the art will appreciated that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein.

DETAILED DESCRIPTION

Figure 1:
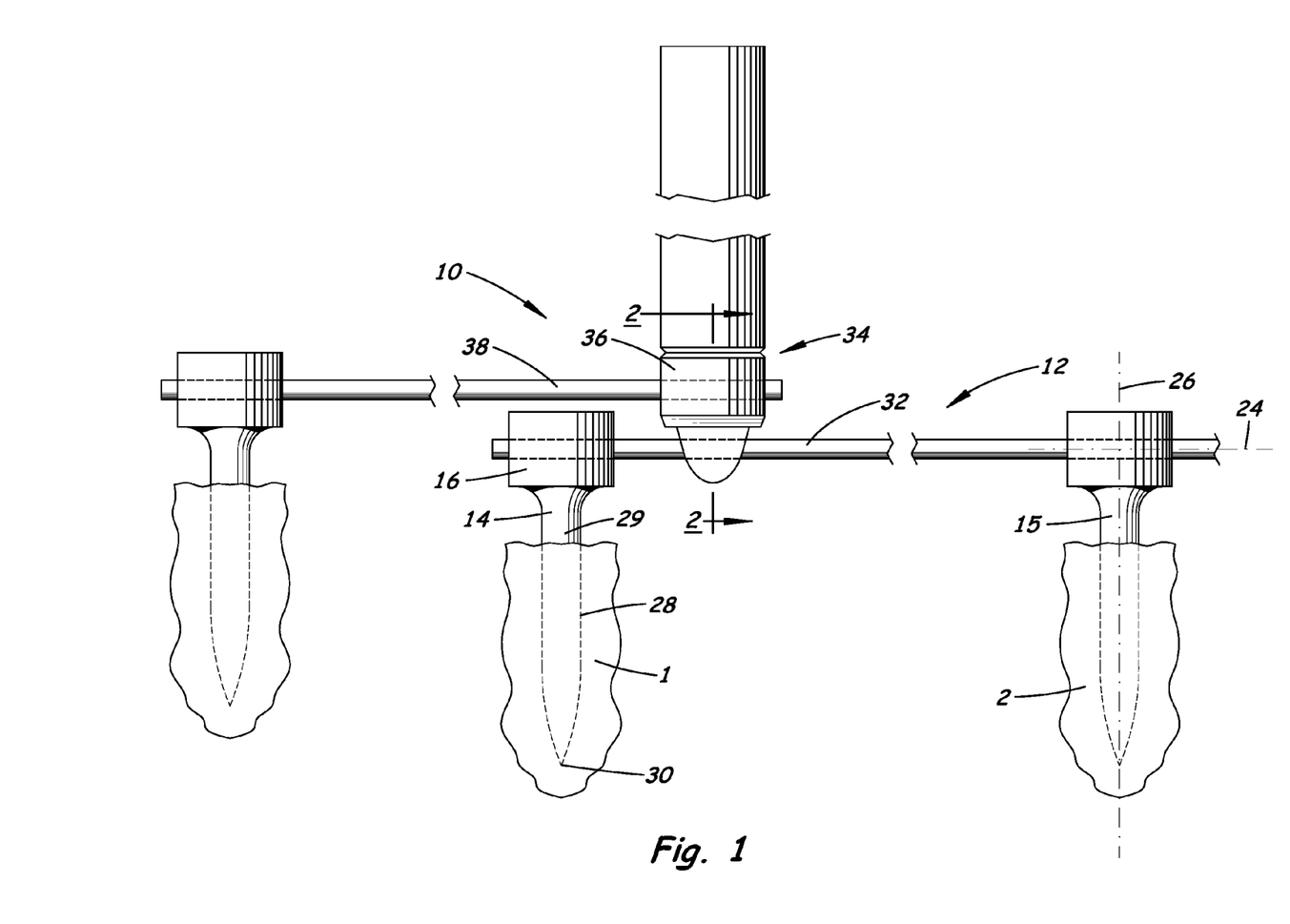
FIG. 1 is a schematic side view of the new system utilizing the rod interface device according to the present disclosure.
Figure 2:
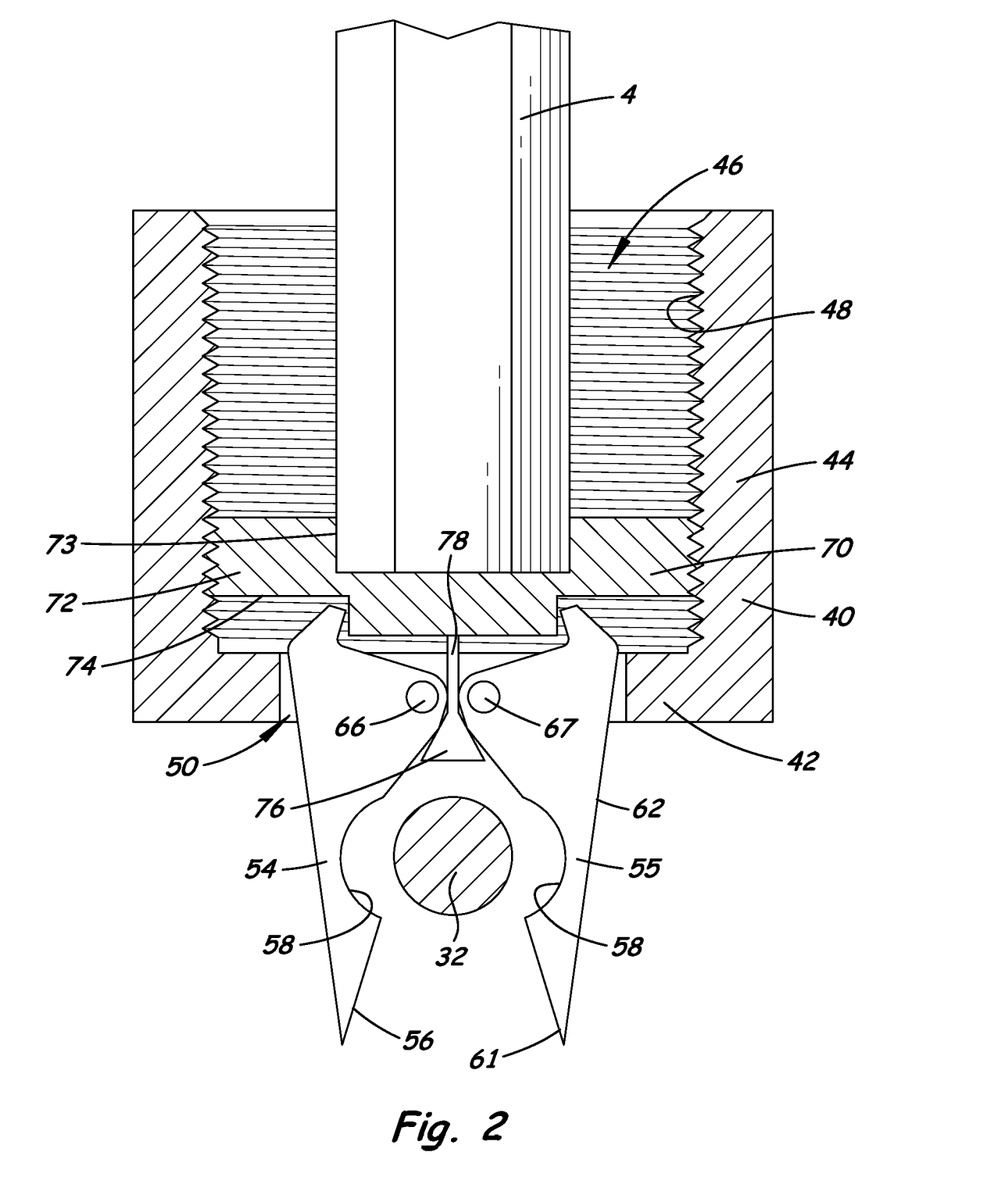
FIG. 2 is a schematic sectional view of the rod interface device of the system, according to an illustrative embodiment, from the perspective of line 2-2 of FIG. 1 with the jaws shown in the release position.
Figure 3:
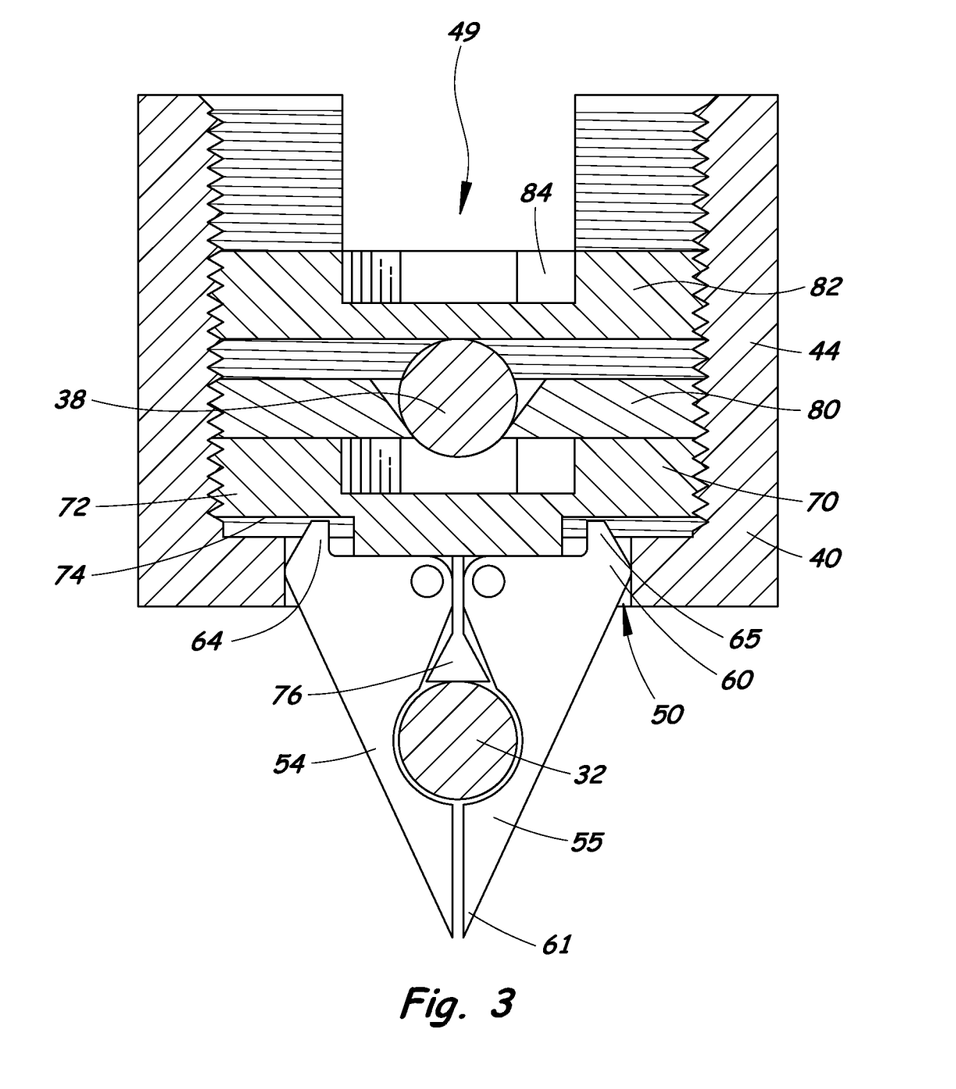
FIG. 3 is a schematic sectional view of the rod interface device of the system, according to an illustrative embodiment, from the perspective of line 2-2 of FIG. 1 with the jaws shown in the gripping position.
Figure 4:
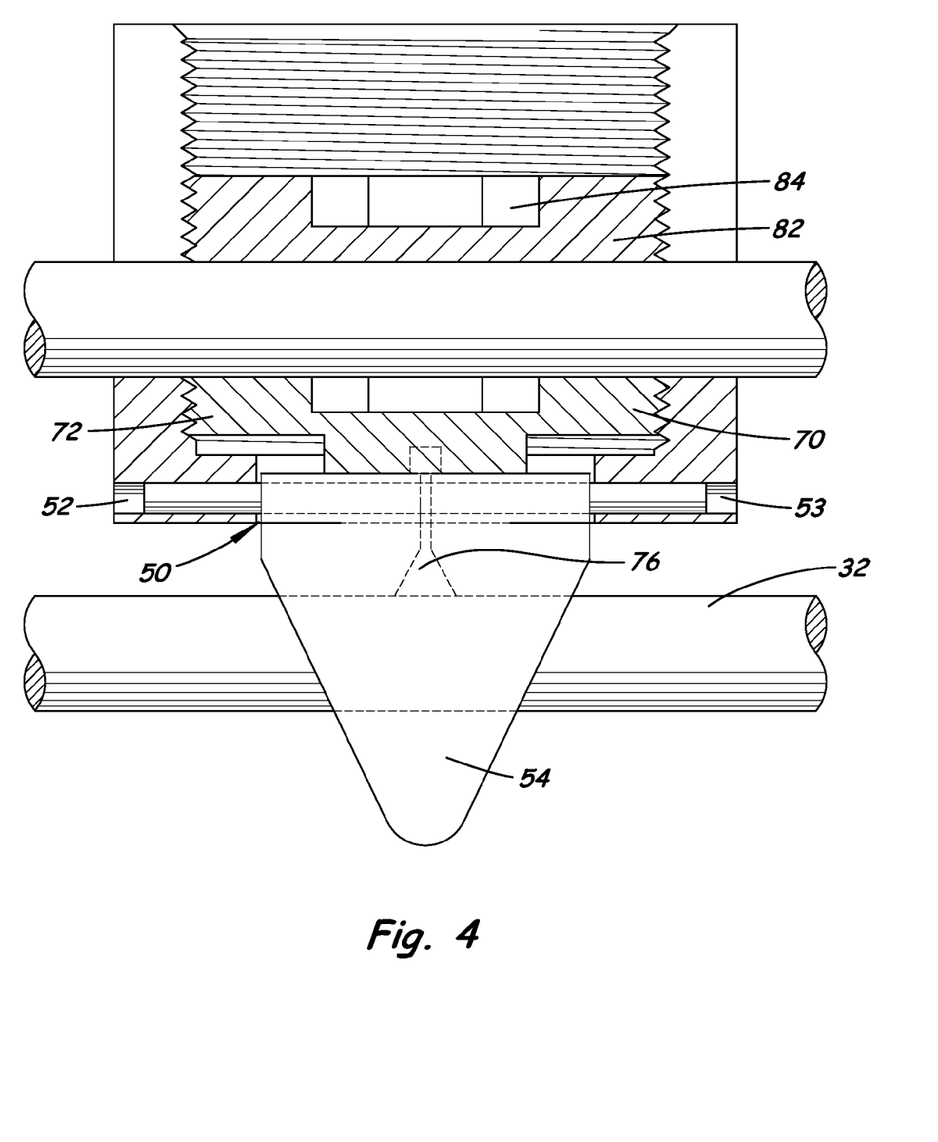
FIG. 4 is a schematic sectional view of the rod interface device taken along a plane substantially perpendicular to plane of the sections shown in FIGS. 2 and 3, according to an illustrative embodiment.
Figure 5:
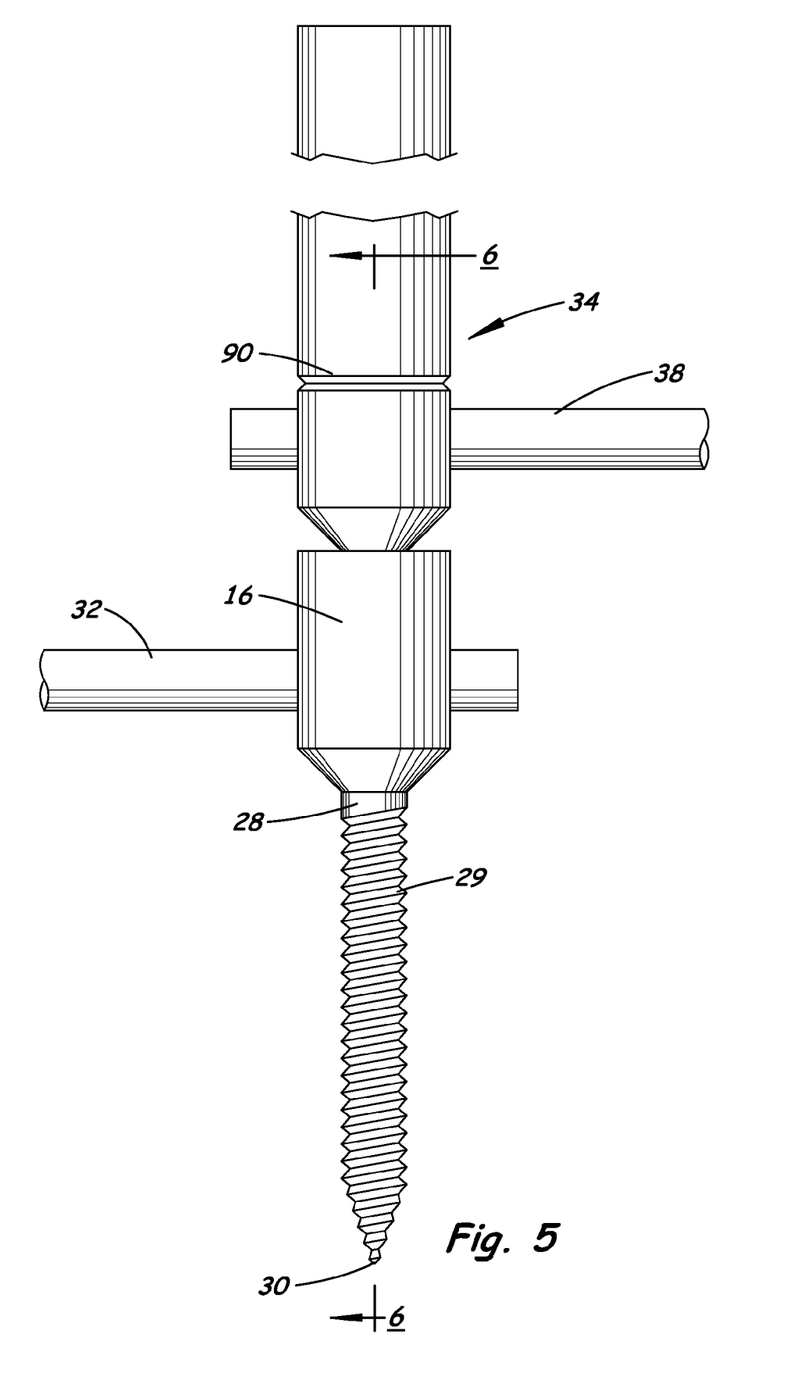
FIG. 5 is a schematic side view of an illustrative embodiment of the system utilizing a screw interface device.
Figure 6:
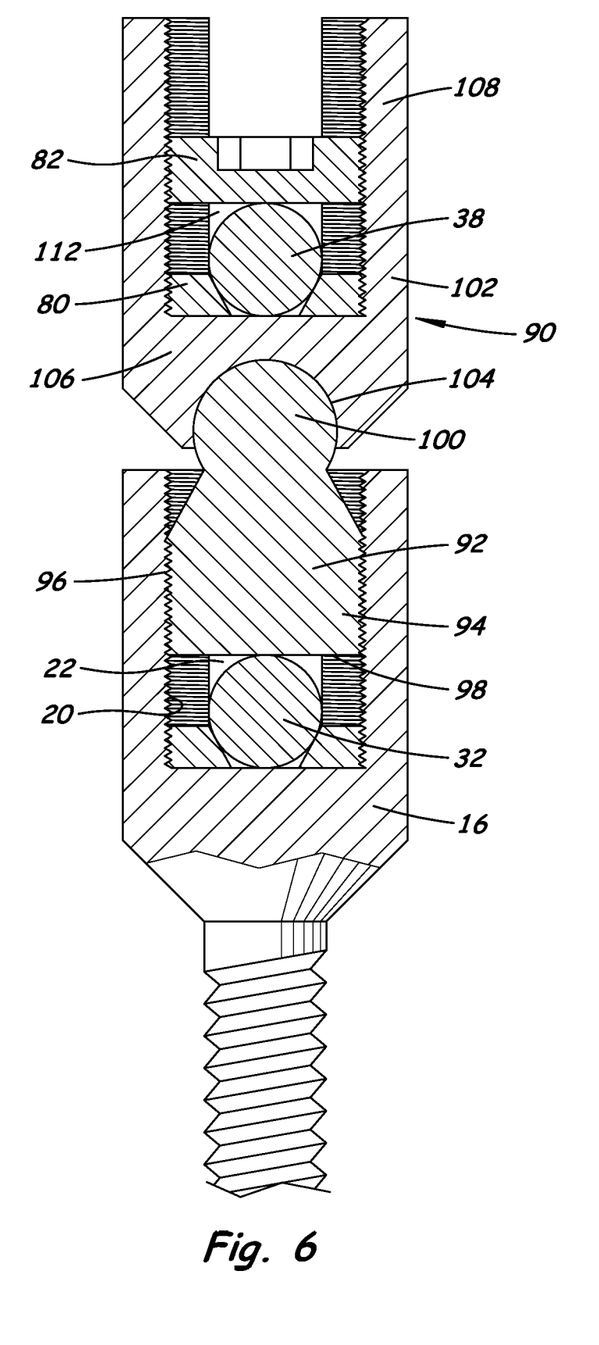
FIG. 6 is a schematic side sectional view of the screw interface device, according to an illustrative embodiment, from a perspective taken along line 6-6 of FIG. 5.
Figure 7:
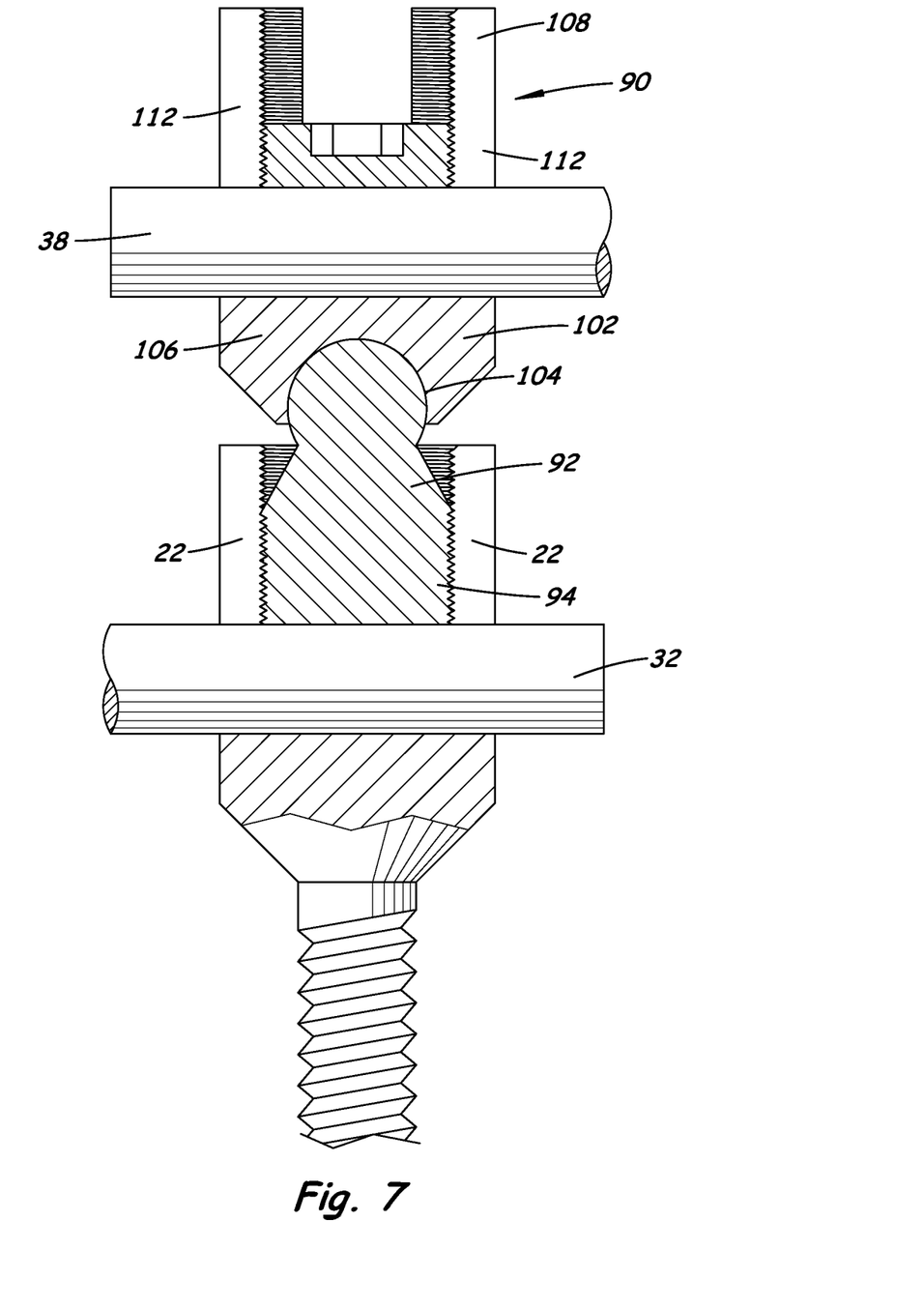
FIG. 7 is a schematic sectional view of the screw interface device taken along a plane substantially perpendicular to the plane of the sections show in FIG. 6, according to an illustrative embodiment.

With reference now to the drawings, and in particular to FIGS. 1 through 7 thereof, a new system and method for lengthening an existing spinal support structure embodying the principles and concepts of the disclosed subject matter will be described.

Spinal surgeries, and especially spinal fusion surgeries, utilize a bone graft to fuse the adjacent vertebrae. Often metal screws are mounted on the vertebral body, and a rod or rods are secured to the screws, to hold the vertebrae in place while the spine fusion heals. The screws are mounted on the pedicle portion of the vertebra, which forms the small bony tube for the spinal cord, to grab into the bone of the vertebral body for a solid anchoring on the vertebra. After the screws are mounted, with one in each pedicle, the rod or rods are attached to connect all the screws together to create a relatively rigid metal frame that holds the vertebrae in position with respect to each other. A bone grafting material may then be placed around the back of the vertebrae to help heal and fuse the vertebrae together. Increasingly the surgery can be performed in a minimally invasive matter, so that the screws and rods may be placed using a series of small incisions rather than one long incision extending at least the length of the rod or rods.

After a spinal fusion surgery has been performed, the spinal discs adjacent to the fused discs may have increased pressure and may fail, requiring spinal fusions at additional levels of the spine in surgery generally referred to as revision spine surgery. Applicant has recognized that unlike the initial spinal fusion surgery, the revision surgery may not be able to be performed in a minimally invasive manner, such as by substituting a longer rod to reach the additional spinal vertebra levels. Applicant has further recognized that it would be advantageous to avoid revision surgery that utilizes the conventional practice of making a full-length incision to remove the existing rod, install pedicle screws on the additional vertebrae levels, and then install a new longer rod mounted to the existing and new screws.

In one aspect, the disclosure relates to a system 10 for adding or integrating one or more rods to an existing rod and pedicle screw installation, such as an installation from a previous spinal surgery. In some embodiments, connection of the additional rod is made to the rod previously implanted in the patient, and in some embodiments the connection of the additional rod is made to a pedicle screw of a previous surgery. The implantation and assembly of the elements of the system may be conducted in a minimally-invasive manner, generally without forming a large incision in the tissue of the patient and instead may be conducted through small incisions. Removal of the existing spine support structure including any rods and screws, is not typically needed for implementation of the system 10.

In some embodiments, the system 10 may include an existing spine stabilization structure 12 that has previously been implanted in the patient and my be attached to the spine of the patient. The existing spine stabilization structure 12 may include a pair of pedicle screws 14, 15 that are configured for threaded insertion into the vertebra 2, 3 of the patient, with each of the pedicle screws being mounted on the pedicle of a vertebra of the patient. The particular configuration of the screw is not critical as long as the screw is suitable for the purpose. An illustrative suitable screw will be described.

Each of the pedicle screws 14, 15 may include a head portion 16 which defines a cavity 18. The cavity 18 may be defined or bounded by inner surface 20 which may have threads formed thereon for purposes that will become apparent. A channel 22 may be formed in the head portion 16 and may extend through the cavity 18 for receiving a portion of a rod therein. The channel 22 may extend along a transverse axis 24 that is oriented substantially transverse to a longitudinal axis of the pedicle screw. The screws 14, 15 may also include a body portion 28 that is connected to the head portion either rigidly or in a manner permitting some relative movement therebetween. The body portion may be configured to be threaded into a hole formed in the vertebra, and at least a portion of the exterior surface 29 may be threaded. The body portion 28 may terminate in a tip 30. The existing spine stabilization structure 12 may further include an existing rod 32 that extends between the pedicle screw 14, 15 with a portion of each existing rod being lodged in the channel 22 of each of the head portions 16 of the respective pedicle screws.

The system may also include an interface structure 34 that is configured to link an additional rod to another rod, such as a rod that was placed in a previous surgery. The interface structure 34 may be placed in a minimally-invasive manner, although a minimal invasive installation is not required.

In some embodiments of the system, the interface structure 34 may comprise a rod interface device 36 that is configured to connect an additional rod 38 to an existing rod 32. The rod interface device may include a frame 40 that has a bottom wall 42 and a perimeter wall 44 that extends upwardly from the bottom wall to partially define an interior 46 of the frame. The perimeter wall 44 may have an inward surface 48 with threads formed thereon. A pair of opposed grooves 49 may be formed in the perimeter walls to receive the additional rod therein. An opening 50 may be formed in the bottom wall 42 and the bottom wall may have a pair of cavities 52, 53 that are positioned at opposite locations on the opening 50 in opposition to each other. The grooves 49 in the perimeter wall may form a pair of perimeter wall portions that are located on opposite sides of the frame, and in some of the most preferred embodiments the perimeter wall portions may be elongated to help guide the movement of the device elements, tools, as well as other things into the operative area (such as through an incision in the body of the patient). These elongate perimeter wall portions, which are illustratively shown in FIGS. 1 and 5, may have a score line or line of reduced thickness and weakness formed across the portion that allows the perimeter wall portion to be severed or broken at the line, for example, when the device has been implanted. The relative length of the section beyond the line that may be removed may be one to ten or more times the length of the section that remains connected to the bottom wall. The position of the score line on the perimeter wall portions is preferably positioned at a distance from the bottom wall that minimizes the protrusion of the perimeter wall portion more than is necessary to accomplish the functionality of the interface structure. Illustratively, the position of the score line on the perimeter wall portion, and the height of the wall portion, may be sized to minimize the protrusion of the perimeter wall portions beyond, for example, the rod securing element 82.

The rod interface device 36 may further include a pair of gripping jaws 54, 55 that may be configured to releasably grip the existing rod 32 so that the interface device 36 may be attached to the rod 32 in a secure manner. The gripping jaws 54, 55 may be movable with respect to each other between a release position (see FIG. 2) a gripping position (see FIG. 3). The gripping jaws 54, 55 may be mounted to pivot with respect to each other, and may be mounted on the frame 40 in a pivotable manner.

The jaws 54, 55 may have similar or identical configurations, but that is not critical. Each of the gripping jaws may include an inner surface 56 that faces an inner surface of the other jaw, with the inner surfaces being relatively closer together in the gripping position and relatively farther apart in the release position. One or both of the inner surfaces 56 of the jaws 54, may have a recess 58 for receiving a portion of the existing rod 32 and a recess in one inner surface may be positioned in opposition to the recess of the other jaw when the jaws are in the gripping position. In some embodiments, the recess may be substantially semi-cylindrical in shape, although other shapes may be employed. The inner surface of the jaws may be generally planar about the recess. The jaws 54, 55 may have an inboard end 60 positioned relatively closer to the frame 40, an outboard end 61 positioned relatively farther from the frame. The jaws 54, 55 may have an outer surface 62 that tapers smaller toward the outboard end and larger toward the inboard end such that a relatively smaller tip is created that facilitates insertion of the jaws and frame into an incision in the body, and the tapered shape of the outer surface of a jaw may have a semi-conical shape.

Each of the gripping jaws 54, 55 may include closing tab 64, 65 that may extend from the respective jaw at the inboard end and may extending in a direction substantially opposite from the outboard end of the jaw. A pair of pivot pins 66, 67 may mount the gripping jaws on the frame 40 in a manner permitting pivot movement of the jaw with respect to the frame. The pivot pins have opposite ends that may be positioned in the cavities 52, 53 of the frame, and each pivot pin may extend through one of the jaws and across the opening 50 of the frame.

The interface structure 34 may further include a jaw manipulation structure 70 that may be configured to move the jaws between the gripping position and the release position in a controllable manner. The manipulation structure 70 may comprise a jaw closer element 72 that may be configured to contact the jaws 54, 55 and move the jaws toward the gripping position. The jaw closer element 72 may be mounted on the frame 40 and may be rotatable with respect to the frame, and in some embodiments a perimeter surface of the jaw closer element may have threads formed thereon to engage the threads on the inward surface 48 of the perimeter wall 44 of the frame. By the engagement of the threads, the jaw closer element may be moved closer to, and away from, the bottom wall 42 of the frame by rotating the closer element in one rotational direction or the other direction. The jaw closer element 72 may have a tool recess 73 formed thereon to receive a portion of a tool 4 to cause rotation of the closer element 72 by the surgeon.

The jaw closer element 72 has an abutment surface 74 that is positioned to be able to contact the closing tabs 64, 65 of the jaws when the closer element is moved toward the bottom wall of the frame, such as by rotation on the threads engaging the perimeter wall of the frame. As the closer element 72 contacts the tabs 64. 65 and the closer element 72 is moved closer toward the bottom wall the abutment surfaces presses against the tabs and moves the tabs toward the bottom wall and also outwardly relative to each other. The effect on the jaws is to pivot the jaws toward the gripping position, with the outboard ends 61 moved toward each other as well as the inner surfaces 56 and the recesses 58 of the jaws. The movement of the jaws toward the gripping position allows the recesses to close in upon a rod 32 that is located between the jaws, and may effectively trap the rod between the jaws and secure the frame to the rod.

The jaw manipulation structure 34 may also include a jaw spreader element 76 that may be configured to move the jaws toward the release position when in a first relationship (see FIG. 2) with the jaws and to permit the jaws to move toward the gripping position when in a second relationship (see FIG. 3) with the jaws. Three spreader element 76 may have a tapered shape, and in some embodiments may have a substantially conical shape that is inverted when the interface structure 34 is positioned above a rod for coupling.

The jaw spreader element 76 may be moveable with respect to, and between the jaws. The jaw spreader element may be rotatable with the jaw closer element 72 such that movement of the closer element 72 with respect of the frame also moves the spreader element with respect to the frame. The jaw manipulation structure 34 may further comprise a jaw connector element 78 that may connect the jaw spreader element 76 to the jaw closer element such that movement of the jaw closer element is transferred to the jaw spreader element. The transferred movement may include translational movement as well as rotational movement. The jaw connector element may extend between the jaws. In some embodiments, the jaw closer element, the jaw connector element and the jaw spreader element are formed of a single piece of material.

In a general sense, movement of the closer element toward the bottom wall 42 moves the spreader element away from the wall 42 and movement of the closer element away from the wall 42 moves the spreader element toward the wall 42. Movement of the jaw spreader element toward the bottom wall causes contact of the outer surface of the spreader element with the inner surfaces 56 of the jaws and the tapered shape of the spreader element tends to push the inner surfaces away from each other and pivot the outboard ends of the jaws away from each other, opening the jaws toward the release position, as the tapered spreader element wedges between the jaws. Movement of the jaw spreader element away from the bottom wall 42 allows the inner surfaces of the jaws to move toward each other, especially in conjunction with the movement of the abutment surface 74 of the jaw closer element against the closing tabs 64 of the jaws. As the jaw closer element moves closer to the bottom wall, and the jaw spreader element moves away from the bottom wall, the jaws are moved toward the gripping position.

The rod interface device 36 may also include a rod seating element 80 for stabilizing the position of the additional rod 38 when positioned in the frame interior and passing through the channel 22. The rod seating element 80 may be positioned in the interior of the frame, and may be positioned adjacent to the jaw closer element 72 of the jaw manipulation structure 70 with the rod 38 abutted against the device 36. The rod seating element 80 may have a midsection of tapered thickness with an outer section of thicker thickness relative to the midsection to tend to center the rod 38 toward the center of the channel. A rod securing element 82 may be positioned in the interior of the frame, and may have an outer peripheral surface formed with threads to engage the threads on the inward surface 48 of the frame. The rod securing element may have a tool recess 84 for receiving a tool to rotate the rod securing element to tighten the abutment of the securing element 82 against the rod 38 as well as loosen the abutment if desired.

Methods of using the system 10 with the rod interface device 36 may include steps of locating a location on the existing rod where the additional rod is to be connected to the existing rod, forming an incision in the patient to access the location on the existing rod, and moving the rod interface device through the incision to the location in the existing rod. While moving the rod interface device yp the location, the jaws may preferably be in the gripping position such that the jaws present a relative tapered profile to the tissue on the sides of the incision. The jaws are placed in the gripping position by moving the jaw closer element 76 toward the bottom wall 42 by rotating the jaw closer element, which in turn presses the abutment surface 74 against the closing tabs 64, 654 of the jaws. Once the rod interface device is positioned close the existing rod, the jaw may be moved toward the release position by rotating the jaw closer element on the threads in a manner that moves the closer element away from the bottom wall, which in turn moves the jaw spreader element toward the bottom wall, and wedges the spreader element 76 between the jaws and tends to rotate the jaws toward the release position. Once the outboard ends of the jaws are suitable spread, then the rod interface device may be advanced toward the existing rod 32 to move the rod 32 between the jaws and into the recesses 58 of the jaws. Once the rod 32 has sufficiently moved into position between the recess, the jaws closer element may be rotated in a direction that moves the closer element on the threads toward the bottom wall, bringing the abutment surfaces against the closing tabs, and moving the jaw spreader element away from the bottom wall and out of the wedged relationship with the jaws. The outboard ends of the jaws tend to move toward each other each other, trapping the existing rod in the recesses or, and between, the jaws.

The rod seating element 80, if utilized, may be positioned adjacent to the jaw closer element, and a portion of the additional rod 38 may be positioned in the grooves 49 of the perimeter wall of the frame such that the rod portion passes through at least a portion of the interior of the frame. The additional rod may be inserted into the operative area through known minimally-invasive techniques. The rod securing element 82 may be threaded into the interior of the frame by rotating and brought into abutment with the rod with sufficient pressure to hold the rod against the rod seating element and/or jaw closer element.

In some embodiments of the system 10, the interface structure 34 may comprise a screw interface device 90 that is configured to connect the additional rod 38 to an existing screw 14. The screw interface device 34 may be configured to be connected to the head portion of a pedicle screw, and in particular a pedicle screw that includes a perimeter wall with threads formed on at least a portion of the inward surface of the perimeter wall. The screw interface device 90 may include a screw mount element 92 that is configured to be mounted on the head of the pedicle screw, such as the existing pedicle screw of a previous surgery with an existing rod 32 remaining in place. More specifically, the screw mount element may be mountable on the head portion 16 of the screw, such as by insertion of a portion of the mount element 92 into the cavity 18 and enging the threads formed on the inner surfaces 20 of the head portion.

The screw mount element 92 may include a first mount portion 94 that has a threaded outer surface 96 for engaging the threads of the inner surface of the head portion of the screw. The outer surface 96 of the first mount portion 94 may be substantially cylindrical with the threads thereon such that engagement between the respective threads causes the first mount portion to move into the cavity 18 of the head portion as the mount element or at least the first mount portion is rotated. The first mount portion 94 may be employed to press and secure the existing rod 32 into the cavity 19 and the channel 22 by contact with a lower surface 98 of the mount portion with the rod 32. The screw mount element 92 may include a second mount portion 100 that extends from the first mount portion 94, and may have a partially spherical surface.

The screw mount element may also include a rod mount element 102 that is mounted on the screw mount element 92 and may be mounted on the rod mount element in a manner permitting movement of the rod mount element in a manner permitting movement of the rod mount element with respect of the screw mount element, although this is not critical. The rod mount element 102 may define a cavity 104 that receives a portion of the second mount portion 100 of the screw mount element, and the internal surface defining the cavity may be at least partially spherical in shape to engage the surface of the second mount portion. The rod mount element 102 may also include a lower wall 106 within the cavity 104 formed therein and a side wall 108 extending upwardly form the lower wall. The lower and side walls may define a pocket 110 for receiving the additional rod therethrough, and the side walls may have a pair of opposed notches 112 through which the rod extends into and out of the pocket. A rod seating element may be located in the pocket 110, and a rod securing element may also be positioned in the pocket to engage the threads and abut against the additional rod to hold the rod in the pocket Methods of using the system 10 with the screw interface device 90 may include steps of locating a location of an existing screw 14 to which the additional rod is to be connected, forming an incision in the patient to access the location of the screw, and moving the screw interface device through the incision in the patient to the location adjacent to the screw, such as the head portion of the screw. An existing screw element may be removed from the head portion of the screw prior to insertion of the interface device 90, but in some implementations that securing element may be left in place if sufficient room remains in the cavity for a section of the first mount portion 94 of the screw mount element 92. A section of the first mount portion may be threaded into the cavity and may be rotated to a degree that the screw mount engages the existing rod if an existing rod has been removed. Once the screw mount element has been secured to the head portion of the screw, a rod seating element may be inserted into the pocket and then the additional rod may also be inserted into the pocket and then the additional rod may also be inserted into the pocket 110 and through at least one of the pair of opposed notches 112 of the rod mount element 102. The additional rod may be inserted into the operative area through known minimally-invasive techniques. A rod securing element may be inserted into the pocket and engaged with the threads by rotation, with rotation continuing until the rod securing element places sufficient pressure against the rod to securely anchor it in place.

It should be appreciated that the foregoing description and appended claims that the terms substantially, mean "for the most part" or "being largely but not wholly or completely that which is specified" by the modified term.

It should also be appreciated from the foregoing description that, except when mutually exclusive, the features of the various embodiments described herein may be combined with features of other embodiments as desired while remaining within the intended scope of the disclosure.

Further, those skilled in the art will appreciate that the steps shown in the drawing figures may be altered in a variety of ways. For example, the order of the steps may be rearranged, substeps may be performed in parallel, shown steps may be omitted, or other steps may be included, etc.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

What is claimed is:

1. An implantable device comprising:
   a spinal rod support having a perimeter structure forming a threaded interior cavity and the perimeter structure including opposed channels forming a first passage for a first spinal rod into the interior cavity; and
   a pair of gripping jaws movably coupled to the spinal rod support and movable relative to each other between an open position and a closed position to grip and release a second spinal rod, the gripping jaws forming a second passage for the second spinal rod, each gripping jaw having an outer surface, the gripping jaws having a width dimension extending from a proximal end of the jaws to a distal end of the jaws to define a substantially semi-conical shape on each gripping jaw outer surface.

2. The implantable device of claim 1 comprising a threaded securing element sized to threadably engage the threaded interior cavity of the perimeter structure to secure the first spinal rod to the spinal rod support.

3. The implantable device of claim 1 wherein the jaws are movably coupled to the spinal rod support through a pair of pivot pins to rotate between the open position and the closed position.

4. The implantable device of claim 1 wherein the gripping jaws are pivotally coupled to a bottom structure of the spinal rod support to rotate inwardly to the closed position and outwardly to the open position and the jaws are supported in a bottom opening of the spinal rod support so that a proximal end of the gripping jaws are adjacent to the interior cavity and a distal end of the gripping jaws are spaced from the spinal rod support.

5. The implantable device of claim 4 wherein the jaws are pivotally coupled to the bottom structure of the spinal rod support through one or more pivot pins having opposed ends connected to the bottom structure and a length extending through the bottom opening.

6. The implantable device of claim 1 wherein the pair of gripping jaws have a length dimension that is parallel to an axis of the second passage, wherein the length dimension of the jaws has a tapered profile to provide a longer length dimension at the proximal end of the jaws and a shorter length dimension at the distal end of the jaws.

7. The implantable device of claim 1 wherein the jaws include an inner surface and the inner surface is contoured to form the second passage, the second passage being generally cylindrically shaped.

8. The implantable device of claim 1 wherein the jaws are pivotally connected to the spinal rod support and comprising means for rotating the jaws from the open position to the closed position.

9. The implantable device of claim 1 wherein the jaws are pivotally connected to the spinal rod support and comprising means for rotating the jaws from the closed position to the opened position.

10. The implantable device of claim 1 wherein the jaws are pivotally connected to the spinal rod support to rotate inwardly to close the jaws and outwardly to open the jaws and comprising a threaded insert sized for insertion into the threaded interior cavity and rotatable to move the insert towards a bottom of the spinal rod support to engage the jaws through a bottom opening to rotate the jaws inwardly to the closed position.

11. The implantable device of claim 10 and comprising a spreader structure coupled to the insert and rotatable therewith, and the insert is rotated in a first direction to close the jaws and rotated in a second opposite direction to open the jaws.

12. The implantable device of claim 11 wherein the jaws include inner surfaces and the spreader structure includes a tapered surface aligned to contact the inner surfaces of the jaws to rotate the jaws outwardly when the insert is rotated in a second direction.

13. The implantable device of claim 10 and comprising a tool insertable into a fitting on the threaded insert and the tool is configured to rotate the insert to pivot the jaws between the open position and the closed position.

14. A kit comprising:
    a spinal rod; and
    a spinal rod support including a head having an internally threaded perimeter structure forming a threaded cavity and the perimeter structure including opposed channels forming a first passage for the spinal rod into the threaded cavity and a pair of gripping jaws movably coupled to the head and movable relative to each other between an open position and a closed position and rotationally coupled to the head through pins to rotate outwardly to an open position and rotate inwardly to a closed position to grip and release an implanted second spinal rod and comprising a threaded insert rotatable in the threaded cavity between a first position spaced from the gripping jaws and a second position abutting the gripping jaws to rotate the jaws inwardly to the closed position and a spreader element coupled to the threaded insert and rotatable therewith wherein the gripping jaws include an inner surfaces and the spreader element includes ramped surfaces movable along the inner surfaces of the gripping jaws to rotate the jaws outwardly to the open position when the threaded insert is in the first position.

15. The kit of claim 14 wherein the jaws have a tapered profile extending from a proximal end of the jaws to a distal end of the jaws spaced from the head of the spinal rod support.

* * * * *